United States Patent [19]
Albericio et al.

[11] Patent Number: 5,777,077
[45] Date of Patent: Jul. 7, 1998

[54] AUTOMATED ALLYL DEPROTECTION IN SOLID-PHASE SYNTHESIS

[75] Inventors: Fernando Albericio. Boston; Steven A. Kates. Newton. both of Mass.

[73] Assignee: PerSeptive Biosystems, Inc.. Framingham. Mass.

[21] Appl. No.: 803,557

[22] Filed: Feb. 20, 1997

Related U.S. Application Data

[63] Continuation of Ser. No. 324,370, Oct. 17, 1994, abandoned, which is a continuation of Ser. No. 45,273, Apr. 5, 1993, abandoned.

[51] Int. Cl.$^6$ ........................................... C07K 1/06
[52] U.S. Cl. .................. 530/335; 530/333; 530/334; 530/337; 530/340
[58] Field of Search ........................ 530/333, 334, 530/335, 336, 337, 340

[56] References Cited

U.S. PATENT DOCUMENTS

| | | | |
|---|---|---|---|
| 4,314,942 | 2/1982 | McCombie | 540/310 |
| 4,870,199 | 9/1989 | Chen | 556/437 |
| 4,929,671 | 5/1990 | Kunz et al. | 525/54.11 |
| 5,124,448 | 6/1992 | Tschaen et al. | 540/221 |
| 5,214,195 | 5/1993 | Kung et al. | 560/157 |
| 5,324,786 | 6/1994 | Kunz et al. | 525/302 |

FOREIGN PATENT DOCUMENTS

| | | | |
|---|---|---|---|
| 0518295 | 12/1992 | European Pat. Off. | C07K 1/06 |
| WO 91/01331 | 2/1991 | WIPO | C07K 7/54 |
| WO 92/19643 | 11/1992 | WIPO | C07K 1/06 |

OTHER PUBLICATIONS

Stevens and Watanabe. "Amino Acid Derivatives. I. Carboallyloxy Derivatives of α–Amino Acids." *J. Am. Chem. Soc.*, 72:725–727 (Jan.–Apr. 1950).

Corey and Suggs. "Selective Cleavage of Allyl Ethers Under Mild Conditions by Transition Metal Reagents." *J. Org. Chem.* 38 (18) :3224 (1973).

Kunz and Dombo. "Solid Phase Synthesis of Peptides and Glycopeptides on Polymeric Supports with Allylic Anchor Groups." *Angew. Chem. Int. Ed. Engl.* , 27 (5) : 711–713 (1983).

Kunz and Waldmann. "The Allyl Group as Mildly and Selectively Removable Carboxy–Protecting Group for the Synthesis of Labile O–Glycopeptides." *Angew. Chem. Int. Ed. Engl.* , 23 (1) : 71–72 (1984).

Guibe, et al.. "Palladium–Catalyzed Reaction of Tributyltin Hybrid. Selective and Very Mild Deprotection of Allyl and Allyloxycarbonyl Derivatives of Amino–Acids." *Tetrahedron Letters*, 27(21):2365–2368 (1986).

Dangles. et al.. "Selective Cleavage of the Allyl and Allyloxycarbonyl Groups through Palladium–Catalyzed Hydrostannolysis with Tributyltin Hybride. Application to the Selective Protection–Deprotection of Amino Acid Derivatives and in Peptide Synthesis." *J. Org. Chem.*, 52:4984–4993 (1987).

Deziel. "Mild Palladium (O) –Catalyzed Deprotection of Allyl Esters. A Useful Application in the Synthesis of Carbapenems and Other β–Lactam Derivatives." *Tetrahedron Letters*, 28(38) :4371–4372 (1987).

Kunz. "Synthesis of Glycopeptides. Partial Structures of Biological Recognition Components." *Angew. Chem. Int. Ed. Engl.* , 26:294–308 (1987).

Kunz et al.. "Allyl Ester as Temporary Protecting Group for the β–Carboxy Function of Aspartic Acid." *Int. J. Peptide Protein Res.* 26:493–497 (1985).

Friedrich–Bochnitschek. et al.. "Allyl Esters as Carboxy Protecting Groups in the Synthesis of O–Glycopeptides." *J. Org. Chem.*, 54:751–756 (1989).

Baldwin. et al.. "Asymmetric Amino Acid Synthesis: Preparation of the β–Anion Derived from Aspartic Acid." *J. Chem. Soc. Perkin Trans.* , 833–834 (1989).

Baldwin. et al.. "Non–Proteinogenic Amino Synthesis: Synthesis of β, γ–Unsaturated α–Amino Acids from Aspartic Acid." *Tetrahedron Letters*, 45(19) :6319–6330 (1989).

Guibe et al.. "Use of an Allylic Anchor Group and of its Palladium Catalyzed Hydrostannolytic Cleavage in the Solid Phase Synthesis of Protected Peptide Fragments." *Tetrahedron Letters*, 30: (20) :2641–2644 (1989).

Xaus. et al.. "An Enzymatic Approach to the Synthesis of Convenient Aspartic Acid Intermediates in Peptide Chemistry. Synthesis of N–Benzyloxycarbonyl–L–Aspartic Acid β–Allyl Esters." *Tetrahedron Letters*, 45(23) : 7421–7426 (1989).

(List continued on next page.)

*Primary Examiner*—Cecilia J. Tsang
*Assistant Examiner*—David Lukton
*Attorney, Agent, or Firm*—Testa. Hurwitz & Thibeault. LLP

[57] ABSTRACT

A method for removing an allyl protecting group from an allyl-protected derivative of a biologically relevant amino acid is disclosed. One relevant aspect of the method is the use of soluble organometallic catalyst, such as an organopalladium catalyst. Preferably, soluble tetrakistriphenylphosphine palladium (0) is used. The allyl deprotection method now disclosed is suitable for use on an instrument for automated peptide synthesis. Methods of preparing the soluble organometallic catalyst are also disclosed, as are soluble catalyst compositions.

22 Claims, 8 Drawing Sheets

OTHER PUBLICATIONS

Hayakawa, et al., "The Allylic Protection Method in Solid–Phase Oligonucleotide Synthesis. An Efficient Preparation of Solid–Anchored DNA Oligomers," *J. Am. Chem. Soc.*, 112:1691–1696 (1990).

Belshaw, et al., "Chlorotrimethylsilane Mediated Formation of ω–Allyl Esters of Aspartic and Glutamic Acids," *Synthetic Communications*, 20(20) :3157–3160 (1990).

Kunz, "Allylic Anchoring Groups in the Solid Phase Synthesis of Peptides and Glycopeptides," *Innovation and Perspectives in Solid Phase Synthesis* (1990).

de la Torre, et. al., "Improved Method for the Synthesis of o–Glycosylated Fmoc Amino Acids to be used in Solid––Phase Glycopeptide Synthesis (Fmoc =fluoren–9–ylmethoxycarbonyl)," *J. Chem. Soc., Chem. Commun.*, 965–867 (1990).

Barney, et al., "Novel Polyethylene Glycol–Polystyrene (PEG–PS) Graft Supports for Solid–Phase Peptide Synthesis," *Peptides*, pp. 267–268 (1992).

Kates, "A Novel, Convenient, Three–Dimensional Orthogonal Strategy for Solid–Phase Synthesis of Cyclic Peptides," *Tetrahedron Letters*, 34(10) :1549–1552 (Mar. 1993).

Barney, et al., "Biopolymer Syntheses on Novel Polyethylene Glycopolstyrene (PEG –PS) Graft Supports," pp. 603–604. (1992).

Zalipsky, et al., "Preparation and Use of an Aminoethyl Polyethylene Glycol–Crosslinked Polystyrene Graft Resin Support for Solid–Phase Peptide Synthesis," *Solid Phase Methods*, pp. 257–260. (1992).

Lawry & Richardson, Mechanism & Theory in Organic Chemistry, pp. 124–126, 138–139, 144–150 (1976).

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
      ( A ) LENGTH: 8 amino acids
      ( B ) TYPE: amino acid
      ( D ) TOPOLOGY: linear ( i i ) MOLECULE TYPE: peptide ( i i i ) HYPOTHETICAL: YES ( v i ) ORIGINAL SOURCE:
 ( C ) INDIVIDUAL ISOLATE: synthetic peptide ( i x ) FEATURE:
 ( A ) NAME/KEY: Modified-site
 ( B ) LOCATION: 1
 ( D ) OTHER INFORMATION: /label= N- term_prot
  / note= "N-terminal alanine residue is optionally
  protected by a temporary
  9- fluorenylmethyloxycarbonyl group"

( i x ) FEATURE:
 ( A ) NAME/KEY: Modified-site
 ( B ) LOCATION: 2
 ( D ) OTHER INFORMATION: /label=varying_residue
  / note= "position occupied by an alanine (ala),
  methionine (met) or tryptophan (trp) residue"

( i x ) FEATURE:
 ( A ) NAME/KEY: Modified-site
 ( B ) LOCATION: 6
 ( D ) OTHER INFORMATION: /label=side-chain_prot
  / note= "aspartic acid residue with allyl
  side-chain protecting group"

( i x ) FEATURE:
 ( A ) NAME/KEY: Modified-site
 ( B ) LOCATION: 8
 ( D ) OTHER INFORMATION: /label=amid_C-term
  / note= "C-terminal amide"

( x i ) SEQUENCE DESCRIPTION: SEQ ID NO:1:

```
Ala  Xaa  Gln  Lys  Thr  Asp  Thr  Pro
 1              5
```

( 2 ) INFORMATION FOR SEQ ID NO:2:

( i ) SEQUENCE CHARACTERISTICS:
  ( A ) LENGTH: 7 amino acids
  ( B ) TYPE: amino acid
  ( D ) TOPOLOGY: circular ( i i ) MOLECULE TYPE: peptide ( i i i ) HYPOTHETICAL: YES ( v i ) ORIGINAL SOURCE:
  ( C ) INDIVIDUAL ISOLATE: synthetic peptide, tachykinin
  antagonist MEN 10355

( i x ) FEATURE:
  ( A ) NAME/KEY: Modified-site
  ( B ) LOCATION: 2
  ( D ) OTHER INFORMATION: /label= D- amino_acid ( i x ) FEATURE:
  ( A ) NAME/KEY: Modified-site
  ( B ) LOCATION: 4
  ( D ) OTHER INFORMATION: /label= D- amino_acid ( i x ) FEATURE:
  ( A ) NAME/KEY: Modified-site
  ( B ) LOCATION: 5
  ( D ) OTHER INFORMATION: /label= D- amino_acid ( x i ) SEQUENCE DESCRIPTION: SEQ ID NO:2:

```
Tyr  Trp  Val  Trp  Trp  Arg  Asp
 1              5
```

AUTOMATED ALLYL DEPROTECTION IN SOLID-PHASE SYNTHESIS

This is a continuation of application Ser. No. 08/324,370 filed on Oct. 17, 1994, now abandoned, which is a continuation of Ser. No. 08/045,273, filed Apr. 5, 1993, now abandoned.

BACKGROUND

Over the past quarter-century, techniques have been developed and refined for the organic synthesis of diverse molecules of biological relevance. In particular, sophisticated methods have been developed for peptide synthesis. These methods have made possible the chemical synthesis of naturally-occurring peptides of interest for research or therapeutic purposes. In addition, many peptide structures have been synthesized for which there is no known naturally-occurring counterpart. It is now possible to synthetically prepare branched or cyclic peptides, or peptides in which one or more amino acid residues are glycosylated, sulfated, phosphorylated or otherwise derivatized. The state of the peptide synthetic art is reviewed in Barany et al. (1987), 30 INT. J. PEPT. PROT. RES. 705–739 and Fields et al. (1992), in SYNTHETIC PEPTIDES: A USER'S GUIDE, 77–183 (Grant, ed.).

For many years, peptide structures were synthesized manually, a laborious process which required significant levels of expertise and was vulnerable to introduced error. Recently, instruments have been developed for automated peptide synthesis, an advance which significantly expands the range and variety of peptide structures that can be made. Automation allows for the preparation of peptides on a larger scale than could previously be attempted. Automated peptide synthesis instrumentation and software have greatly expanded the accessibility of peptide synthesis to academic and industrial investigators in fields beyond organic synthesis and protein chemistry. Synthesized peptide structures are now used as tools in such diverse fields as nutrition, microbiology, immunology, physiology and medicine.

With the increasing sophistication and variety of peptide synthetic techniques that have been reported, however, there has been an increasing awareness of the many limitations and undesired side-reactions that may be provoked. Many of these are idiosyncratic to a particular synthetic reagent or type of amino acid derivative, and effectively limit the range of conditions and combinations in which such reagents can be used. Many reagent- and amino acid-specific undesired side-reactions are also reviewed in Barany et al. (1987), Id. at 727–730.

Many additional and unexpected limitations and undesired side-reactions have been encountered by those adapting manual peptide synthetic techniques for use on instruments for automated peptide synthesis. Efforts to adapt existing methods of peptide synthesis for use in an automated setting, and to develop new methods uniquely suited for automated instrumentation, are presently ongoing. Many desired techniques for peptide synthesis have thus far proven incompatible with automated instrumentation.

For example, synthetic reactions involving allyl-protected amino acid derivatives have proven poorly adaptable to an automated setting. Removal of the allyl group has proven particularly difficult during automated synthesis, due to the nature and physical characteristics of the catalyst relied upon for allyl deprotection.

SUMMARY OF THE INVENTION

The present invention relates to a method for removing an allyl protecting group from an allyl-protected derivative of a biologically relevant amino acid. The method includes the steps of providing a soluble organometallic catalyst, contacting said catalyst with the allyl-protected amino acid derivative, and incubating the allyl-protected amino acid derivative with said catalyst for a sufficient period of time for the allyl protecting group to be catalytically removed from the amino acid derivative, such that an allyl-deprotected amino acid derivative is obtained. Thereafter, the allyl-deprotected amino acid derivative is separated from the catalyst. Most advantageously, the allyl deprotection method of the present invention is suitable for use on an instrument for automated peptide synthesis. This is in large part due to the discovery, reported herein, of conditions under which the organometallic catalyst is soluble. It is particularly important to achieve homogeneous liquid phase conditions in automated solid phase peptide synthesis reactions, in order to avoid fouling of the solid phase support or introducing back-pressure in the reaction vessel or column of an automated instrument.

In one embodiment, the soluble organometallic catalyst is an organopalladium catalyst. Preferably, an organopalladium (0) catalyst is used. Tetrakistriphenylphosphine palladium (0) is particularly preferred. The present organometallic catalyst is provided in a solvent which includes an organic acid and an acceptor. Suitable organic acids include formic acid, acetic acid, propionic acid and the like. Acetic acid has been shown to be a suitable organic acid for purposes of the present invention. Suitable acceptors include morpholine, N-methylmorpholine, dimedone, N-methylaniline, N,N'-dimethylbarbituric acid. N-methylmorpholine has been shown to be particularly a suitable acceptor. The present organic acid and acceptor can be advantageously included within a chloroform, methylene chloride or benzene solvent. The present catalyst is provided and contacted with the allyl-protected amino acid derivative under an inert atmosphere. The allyl deprotection incubation is also carried out under an inert atmosphere. Satisfactory allyl deprotection results have been obtained when a soluble tetrakistriphenylphosphine palladium (0) catalyst is provided under an inert atmosphere in a chloroform solvent further including about 5% acetic acid and about 2.5% N-methylmorpholine.

The automatable allyl deprotection method disclosed herein may be employed for the deprotection of an allyl-protected derivative of a biologically relevant amino acid that is attached to a solid support. The method is suitable for use with polyethylene glycol-polystyrene graft copolymer supports or polystyrene supports. The allyl-protected derivative of a biologically relevant amino acid may be attached to the solid support through a heterobifunctional handle or linker, such as 5-(4-(9-fluorenylmethyloxycarbonyl) aminomethyl-3,5-dimethoxyphenoxy)valeric acid, 5-|(9-fluorenylmethyloxycarbonyl)aminoxanthen-2-oxy| valeric acid or p-alkoxybenzyl alcohol. Furthermore, the allyl-protected derivative of a biologically relevant amino acid may be present in a synthesized peptide formed of biologically relevant amino acid residues linked together by peptide bonds. Allyl deprotection of such a synthesized peptide may be carried out either before or after cleavage of the peptide from a support. As disclosed herein, the present automatable allyl deprotection method may be used most advantageously in the automated preparation of cyclic peptides, including head-to-tail cyclic peptides, branched peptides and multiple antigenic peptides. Allyl deprotection can be carried out according to the present method irrespective of whether the allyl protective group is present on an alpha carbon functional group or a side-chain functional group of the allyl-protected amino acid derivative.

In a second general aspect, the present invention relates to a method of preparing a soluble organopalladium catalyst. The present method includes the steps of providing a solid organopalladium compound, such as tetrakistriphenylphosphine palladium (0), providing a solvent comprising an organic acid and an acceptor in which inert conditions have been established by contacting the solvent with a source of inert gas, and combining the solid organopalladium compound with the solvent under an atmosphere of inert gas, such that a mixture is formed. This mixture is incubated and maintained under an atmosphere of inert gas for a sufficient period of time for the solid organo palladium compound to be dissolved in the solvent, thereby forming a soluble organopalladium catalyst. The resulting soluble catalyst is well-suited for use in automated peptide synthetic procedures wherein an allyl-protected derivative of a biologically relevant amino acid is used, including the synthesis of cyclic peptides, branched peptides and multiple antigenic peptides. The present catalyst preparation method may be carried out on an instrument for automated peptide synthesis.

In a third general aspect, the invention disclosed herein relates to a soluble organometallic catalyst composition. Preferably, the composition includes an organopalladium compound, such as tetrakistriphenylphosphine palladium (0), dissolved under an inert atmosphere in a solvent having therein an organic acid and an acceptor. Preferably, the solvent is a chloroform solvent having therein acetic acid and N-methylmorpholine. As noted above, the present soluble catalyst represents a significant advance in the art, in that it makes possible the automation of many desired peptide synthetic procedures, including the synthesis of cyclic peptides, branched peptides and multiple antigenic peptides. Indeed, allyl protection is highly desirable even in the synthesis of linear peptides, in that the allyl group provides an additional degree of orthogonality when used in conjunction with other widely-used amino acid protecting groups, such as tert-butyloxycarbonyl groups and 9-fluorenylmethyloxy carbonyl groups. With the present invention, allyl protection chemistry can now be viewed as an alternative strategy to tert-butyloxycarbonyl and 9-fluorenyl-methyloxycarbonyl chemistries for the temporary protection of alpha amino groups during the linear elongation of synthetic peptides.

DETAILED DESCRIPTION OF THE PREFERRED EMBODIMENT

Figure 1:
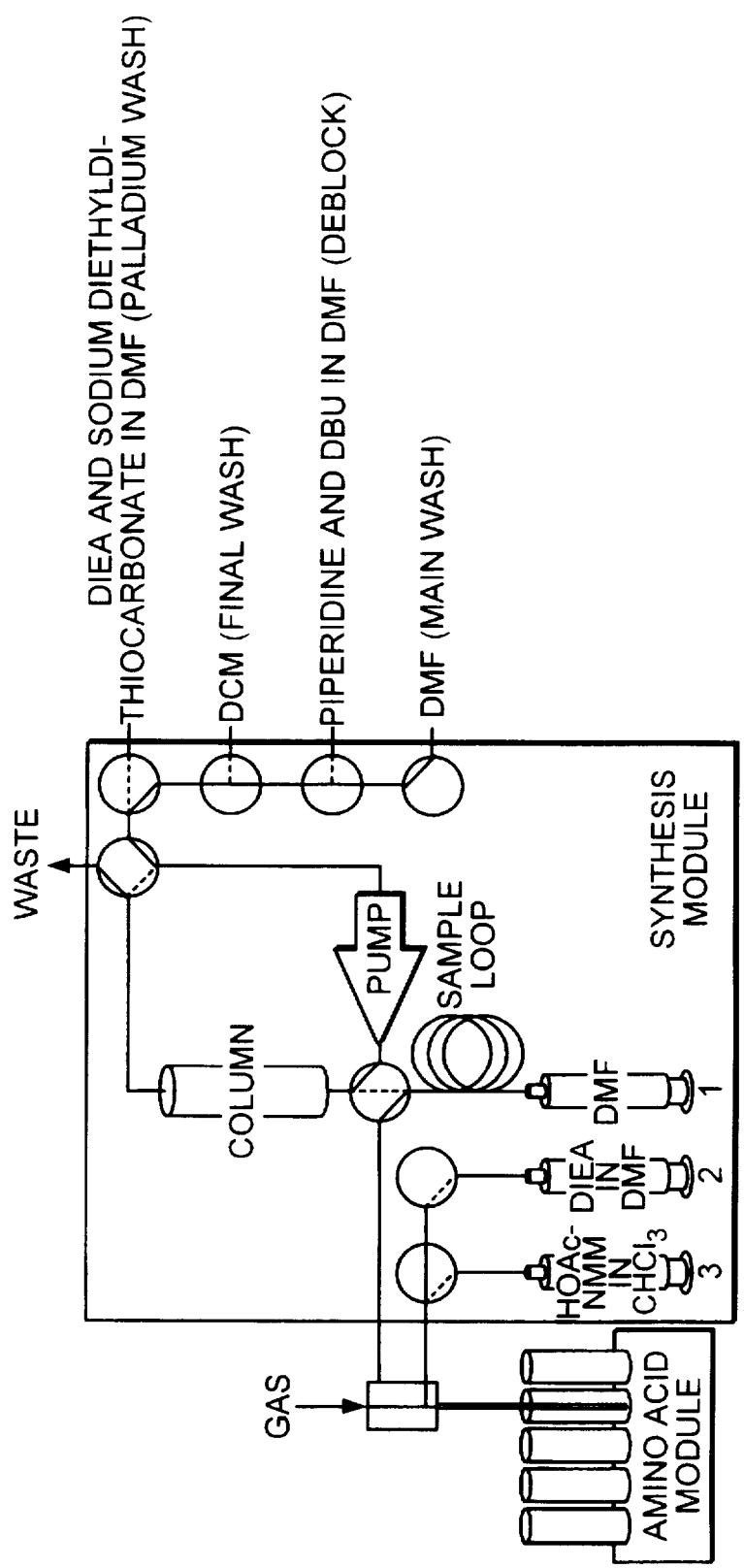
FIG. 1 is a flow diagram of an automated peptide synthesizer configured for automated allyl deprotection according to the present invention.

The present invention capitalizes upon the discovery, noted above, of conditions under which an organometallic catalyst, such as an organopalladium catalyst, for allyl deprotection is soluble. In automated systems for solid phase peptide synthesis, it is important that homogeneous (e.g., liquid phase) reaction conditions be achieved with respect to all components other than the solid support. Thus, the present disclosure of methods of preparing and using a soluble organopalladium catalyst, as well as of the soluble catalyst composition, represent a significant expansion of the breadth of synthetic chemistries suitable for automation. Manual syntheses are, of course, also greatly simplified by the availability of the present soluble catalyst for allyl deprotection.

Allyl protection chemistry is recognized as a desirable tool for use in the synthesis of many complex or labile peptides, but has long been underutilized due to the level of technical expertise required as well as the difficulties of introducing insoluble substances to peptide synthetic reactions and thereafter separating solid byproducts from the desired product. Allyl protection in solid phase peptide synthesis and reagents therefor are disclosed in U.S. Ser. No. 07/715,297, the teachings of which are incorporated herein by reference.

Allyl protecting groups have the general chemical structure

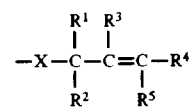

wherein X denotes the site of attachment of the protecting group to a biologically relevant amino acid or derivative thereof, and $R^1$, $R^2$, $R^3$, $R^4$, and $R^5$ are independently selected from the group consisting of: hydrogen, $C_1$–$C_8$ linear or branched alkyl groups, $C_6$–$C_{10}$ aryl groups, $C_1$–$C_8$ linear or branched substituted alkyl groups, and $C_6$–$C_{10}$ substituted aryl groups. The small size of the allyl core structure makes allyl protection desirable in syntheses where steric hinderance is of concern. Thus, smaller substituents, e.g., hydrogen, are preferred for $R^1$, $R^2$, $R^3$, $R^4$, and $R^5$. Allyl groups are desirable for the protection of amino acid sidechains, but can also be used to protect alpha carboxy and amino substituents. Thus, allyl groups can be used for the temporary protection of alpha amino functional groups during the synthesis of a desired peptide.

As noted above, X denotes the site of attachment of the allyl protecting group to a biologically relevant amino acid or a derivative thereof. The amino acids of biological relevance include amino acids naturally occurring in biological systems, e.g., the twenty amino acids found in natural peptides and proteins. That is, alanine, arginine, asparagine, aspartic acid, cysteine, glutamine, glutamic acid, glycine, histidine, isoleucine, leucine, lysine, methionine, phenylanine, proline, serine, threonine, tryptophan, tyrosine and valine are considered biologically relevant amino acids. The present term additionally encompasses amino acid metabolites, e.g., ornithine, which is a component of the urea cycle. Although not so used in natural systems, ornithine may be included in the sequence of a synthesized peptide and subsequently converted into arginine. Both the L- and D-configurations of the foregoing amino acids are encompassed within the present term, although in the following text, the L-configuration is intended unless otherwise specified. Amino acids that are not found in nature but have biological relevance, e.g., that have biological activity, are also included within the present term. Each of the foregoing are abbreviated and designated herein according to the rules of the IUPAC-IUB Commission of Biochemical Nomenclature, set forth in 247 J. BIOL. CHEM. 997–983 (1972), the teachings of which are incorporated herein by reference.

Certain of the biologically relevant amino acids bear side-chain substituents, referred to as functional groups, for which allyl protection may be desirable during peptide synthesis. Thus, the acidic (carboxyl) side-chain functional groups of aspartic acid and glutamic acid, as well as the hydroxyl side-chain functional groups of serine and threonine, along with the phenolic side chain functional group of tyrosine, can be protected by allyl groups. For these amino acids, the immediate site of attachment of the allyl group to the amino acid (X) is an oxygen atom. Allyl protecting groups may similarly depend from a nitrogen atom present in the basic (amino) side-chain functional groups of lysine and ornithine, the amido side-chain functional groups of asparagine and glutamine, the imidazole side-chain functional group of histidine, and the guanidino side-chain functional group of arginine. In like manner, allyl protecting groups can be attached to a sulfur atom present in the sulfhydryl side-chain functional group of cysteine or the thioether side-chain functional group of methionine. Moreover, the foregoing side-chain functional groups can be derivatized with further substitutents of the type found in biological systems, or with substituents that do not occur naturally but are otherwise of interest. Thus, amino acid side-chain functional groups can be sulfated, glycosylated, phosphorylated, iodinated, alkylated, or lipidated.

The present allyl protected derivatives of biologically relevant amino acids are derivatives suitable for solid-phase peptide synthesis. Thus, amino acid derivatives in which one or more functional groups (e.g., the amino substituent of the alpha carbon, referred to herein as the $N^\alpha$ functional group), other than the group protected by an allyl substituent, are protected by a smoothly cleavable temporary protecting group suited to peptide synthetic reactions. Thus, tert-butyl, tert-butyloxycarbonyl, tert-amyloxycarbonyl, adamantanyl-oxycarbonyl, 9-fluorenylmethyloxycarbonyl, 2-(3,5-dimethoxyphenyl)-2-propyloxycarbonyl, dithiasuccinoyl, biphenylylisopropyl-oxycarbonyl, 2,2,5,7,8-pentamethyl-chroman-6-sulfonyl or phenylisopropyloxycarbonyl groups are representative of such temporary protecting groups.

Preferably, the temporary protecting group is one which remains stably attached to the amino acid derivative under a first set of conditions, disclosed herein, used to remove the allyl group, yet which is smoothly released from the amino acid derivative by exposure to a second set of conditions under which the allyl group remains stably attached to the amino acid derivative. This mutual exclusivity of deprotection conditions is referred to as orthogonality. Thus, as described more fully below, allyl protecting groups are orthogonal to tert-butyloxycarbonyl groups and to 9-fluorenylmethyloxycarbonyl groups. Of these, 9-fluorenylmethyloxycarbonyl groups are preferred.

The present amino acid derivatives can be attached to a solid support, e.g., a support for solid-phase peptide synthesis. Suitable supports include resins, membranes, porous glass, silica, polydimethylacrylamides, cotton, paper, polystyrenes and polyethylene glycol-polystrene graft copolymers. Of these, polyethylene glycol-polystyrene graft copolymer supports of the type disclosed by U.S. Ser. No. 07/576,634, now abandoned the teachings of which are incorporated herein by reference, are preferred. Amino acid derivatives are typically attached to the support by covalent bonds. This covalent linkage may be direct or indirect. Thus, an amino acid derivative for solid-phase peptide synthesis may be indirectly linked to the support through a heterobifunctional linking group, also referred to as a handle. The handle serves to enhance steric accessibility of the support-bound amino acid derivative for peptide-synthesis reactions, and is smoothly cleavable upon completion of synthesis. The allyl protecting group can be included within the handle, if employed for the protection of an alpha carboxylic acid substituent during peptide synthesis. Suitable handles or linkers include 5-(4-(9-fluorenylmethyloxycarbonyl) aminomethyl-3,5-dimethoxyphenoxy)valeric acid, 5-|(9-fluorenylmethyloxycarbonyl aminoxanthen-2-oxy| valeric acid and p-alkoxybenzyl alcohol. The handles described in U.S. Pat. No. 5,117,009 and U.S. Pat. No. 5,196,566, the teachings of each of which are incorporated herein by reference, are also suitable.

The present allyl-protected derivative of a biologically relevant amino acid can be present in a synthesized peptide formed of biologically relevant amino acid residues linked together by peptide bonds. The peptide synthesis techniques by which such a peptide is formed are well-known. The techniques described herein provide one representative example of the many synthesis methods and combinations and variations thereof that are available. The present peptide can either be attached to a solid support, or may be soluble. In most instances, it is expected that the peptide will be attached to a solid support. The peptide may be a linear peptide in which peptide bonds link the alpha carbon atoms of a series of amino acid residues, with one terminal amino acid residue having a carboxyl substituent of the alpha carbon (the $C^\alpha$ carboxyl group) either free in solution or linked covalently to a solid support, optionally through a handle as described above. The other terminal amino acid residue of such a linear peptide has an $N^\alpha$ functional group that is either free in solution or protected by a suitable temporary protecting group, such as an allyl group or one of the conventional groups described above. Allyl deprotection of an allyl-protected amino acid derivative present in such a peptide can free the side-chain functional group thereof. Alternatively, the allyl protecting group can be present on either the terminal $N^\alpha$ functional group or the $C^\alpha$ functional group.

Alternatively, the present peptide can be a branched peptide in which at least one additional series of amino acid residues linked together by peptide bonds depends from the side-chain functional group of at least one amino acid residue present in the chain of contiguous peptide bonds originating from the first, support-bound amino acid residue. Thus, peptide branches may depend from both the $N^\alpha$ and side-chain (epsilon, $N^\epsilon$) functional groups of lysine. As described herein, multiply branched structures may be formed from a matrix of lysine residues linked together by peptide bonds at both the $N^\alpha$ and $N^\epsilon$ sites. Such multiply branched structures are described below as multiple antigenic peptides.

As a further alternative, the present peptide can be a cyclic peptide, by which is meant that, e.g., one or both termini of a chain of amino acid residues linked together by peptide bonds may participate in peptide bonds with other amino acid residues in the same peptide. Cyclic peptides can also be formed in which two side-chain functional groups of amino acid substituents present in the same peptide are linked in a peptide bond. Such looped structures can be formed between the side-chains of aspartic or glutamic acid and lysine or ornithine. A stem-and-loop peptide structure can be formed in which the side-chain functional group of one amino acid residue is linked to a terminal $N^\alpha$ or $C^\alpha$ functional group. A head-to-tail cyclic peptide is one in which the terminal carboxy and amino groups have been joined together. A head-to-tail cyclic peptide can be attached to a solid support at the site of a side-chain functional group, e.g., at the side-chain carboxyl group of aspartic acid.

Regardless of whether the allyl-protecting group of such a peptide is present on a side-chain or an alpha terminal functional group, allyl deprotection according to the present invention may precede, follow or otherwise be used in conjunction with procedures for forming cyclic or branched peptide structures, including multiple antigenic peptides.

As summarized above, the present invention capitalizes upon the discovery of conditions under which the catalyst employed for allyl group removal is soluble. In many contemplated embodiments, the present catalyst is an organopalladium catalyst, preferably an organopalladium (0) catalyst. Tetrakistriphenylphosphine palladium (0) [Pd $(PPh_3)_4$] is the preferred catalyst of the present invention. In previously known methods, this catalyst has been used as a suspended solid. Conditions are now described which are suitable for use in peptide synthesis reactions, and under which the preferred catalyst is soluble. Thus, the present invention makes possible the automation of peptide syntheses in which allyl deprotection is required or desired.

It is disclosed herein that the present catalyst can be dissolved in a solvent in which an organic acid and a suitable acceptor are additionally present. Appropriate solvents for tetrakistriphenylphosphine palladium (0) include chloroform, methylene chloride and benzene. Of these, chloroform ($CHCl_3$) is preferred. Dimedone, N-methylaniline, N,N'-dimethylbarbituric acid, morpholine or N-methylmorpholine can be used as acceptors; morpholine and N-methylmorpholine are preferred. N-methylmorpholine (NMM) is particularly preferred in that it has been shown to function as an acceptor without undesired interference with 9-fluorenylmethyloxycarbonyl protection chemistry. Thus, under appropriate conditions, allyl chemistry can be made fully orthogonal to 9-fluorenylmethyloxycarbonyl chemistry. As disclosed herein, N-methylmorpholine is particularly preferred in that it does not exhibit undesired tendencies to act as a base rather than as an acceptor or scavenger for allyl radicals during catalysis. Any suitable organic acid miscible in the present solvent can be used in the present invention. Formic acid, acetic acid and propionic acid can be used; of these, acetic acid (HOAc) has been shown to be particularly suitable.

Thus, in preferred embodiments, tetrakistriphenylphosphine palladium (0) is dissolved in a solvent comprising acetic acid and N-methylmorpholine in chloroform. Acetic acid may be present in this solvent at a concentration between about 3% and about 7%, preferably between about 4% and about 6%, and most preferably at about 5%. N-methylmorpholine may be present therein at a concentration between about 1% and about 4%, preferably between about 2% and about 3%, and most preferably at about 2.5%. Thus, in preferred embodiments, the present catalyst is dissolved in a chloroform solvent further including about 5% acetic acid and about 2.5% N-methylmorpholine.

The soluble organopalladium catalyst of the present invention can be used under normal atmospheric conditions, but is preferably used under an atmosphere of inert gas. Inert conditions are preferably established in the solvent by, e.g., bubbling argon (Ar) gas therethrough prior to contacting the solvent with solid tetrakistriphenylphosphine palladium (0). Inert conditions are thereafter maintained throughout the use of the soluble catalyst for allyl deprotection. Any inert gas can be used to establish an atmosphere of inert gas for the present soluble catalyst.

A sufficient amount of solid organopalladium catalyst is dissolved in the solvent described herein to provide the desired level and rate of allyl deprotection. The proper amount of catalyst will depend on the desired volume and final concentration of soluble catalyst needed for a particular deprotection reaction. The particular type, volume and concentration of allyl-protected amino acid derivative to be deprotected will also influence the amount of solid catalyst to be dissolved in the present solvent. Appropriate levels of catalyst for a particular deprotection reaction can be determined through no more than routine experimentation. Typically, the desired quantity of the soluble organopalladium catalyst of the present invention is calculated as a number of chemical equivalents in excess of the chemical equivalents of allyl protecting groups sought to be removed (deprotected). This practice is followed in the investigative studies and Representative Example set forth below.

The invention described herein, and its significance as an advance in the field of solid-phase synthesis, will be more fully understood in light of the following discussion and illustrative studies.

Emergence of Allyl Protection Chemistry in the Synthesis of Organic and Biochemical Molecules In 1950, Stevens and Watanabe introduced the allyloxycarbonyl (Aloc) group for the protection of amine and alcohol moieties. Stevens and Watanabe (1950), 72 J. AM. CHEM. SOC. 725-727. Cleavage of the Aloc group was accomplished by catalytic hydrogenolysis using platinum or palladium catalysts, the use of metallic sodium in liquid ammonia, or the use of phosphonium iodide in glacial acetic acid (HOAc). Unfortunately, these methods for removal of the Aloc group were not straightforward, limiting the usefulness of this group in organic synthesis. Tsuji and Trost subsequently developed improved reaction conditions for palladium catalyzed allylic deprotection, whereupon the potential of the allyl (Al) protecting group in organic syntheses was recognized. Tsuji (1980), ORGANIC SYNTHESIS WITH PALLADIUM COMPOUNDS, (Springer-Verlag, pub.); Trost (1980), 13 ACC. CHEM. RES. 385-393.

Hayakawa et al. extended the Aloc and allyl group strategy for protection of internucleotide bonds and nucleoside bases in solution- and solid-phase synthesis of nucleic acids. Hayakawa et al. (1990), 112 J. AM. CHEM. SOC 1691-1696. Simultaneous deprotection of the allyl protected phosphates and Aloc protected amine oligomers was accomplished with a mixture of tris(dibenzylideneacetone) dipalladium(0), triphenylphosphine and a large excess of butylamine and formic acid in tetrahydrofuran (THF) at 50° C. for 0.5-1 h.

Guibé et al. investigated the selective cleavage of Aloc and allyl groups for the α-amino and side-chain function: respectively of the biologically relevant amino acids Dangles et al. (1987), 52 J. ORG. CHEM. 4984-4993 Guibé et al. (1986), 27 TETRAHEDRON LETT 2365-2368; Merzouk and Guibé (1992), 33 TETRAHE DRON LETT. 477-480. Guibé studied the effect of differen acceptors as allyl group scavengers and found that the use of tributyltin hydride (Bu$_3$SnH) and silylamines suppressed the formation of undesired allylamine.

Initially, the potential of allyl chemistry was recognized in solid-phase peptide chemistry as a handle which served to attach the growing peptide to the resin. Kunz and Birr introduced the use of 4-bromocrotonic acid coupled to aminomethyl polystyrene resin as an allylic anchor. Kunz and Dombo (1988), 27 ANGEW. CHEM. INT. ED. ENGL. 711–713; Kunz et al. (1988), in PEPTIDES 1988: PROCEEDINGS OF THE TWENTIETH EUROPEAN PEPTIDE SYMPOSIUM 154–156 (Jung and Bayer, eds.); Becker et al. (1988), in PEPTIDES 1988: PROCEEDINGS OF THE TWENTIETH EUROPEAN PEPTIDE SYMPOSIUM 157–159 (Jung and Bayer, eds.). The peptide was detached from the resin by treatment with tetrakistriphenylphosphine palladium(0) [Pd(PPh$_3$)$_4$] in THF and in the presence of an acceptor such as morpholine, dimedone, N-methyaniline or N,N'-dimethylbarbituric acid. With these mild, neutral conditions the preparation of glycopeptides containing sensitive O-glycosidic bonds became possible. Furthermore, Kunz reported the use of N$^\alpha$-terminal 9-fluorenylmethyloxycarbonyl (Fmoc) groups in combination with C-terminal allyl esters as an alternative method for the preparation of O-glycopeptides in solution. Ciommer and Kunz (1991), SYNLETT. 593–595; Friedrich-Bochnistschek et al. (1989), 54 J. ORG. CHEM. 751–756.

Blankemeyer-Menge and Frank described the synthesis of several protected peptide fragments on cellulose disks containing 4-(4'-methoxytrityloxy)-but-2-enyloxyhexanoic acid as an allylic anchor. Blankemeyer-Menge and Frank (1988), 29 TETRAHEDRON LETT. 5871–5874. Deprotection of the allyl ester linkage was achieved by treatment with Pd(PPh$_3$)$_4$ in dry THF followed by the addition of a solution of 1-hydroxybenzotriazole (HOBt) in THF. In order to avoid cleavage of the Fmoc group, HOBt was used as a acceptor rather than morpholine. Guibé and Loffet used 4-trityloxy-but-(Z)-2-enyloxyacetic acid coupled to aminomethyl polystyrene as an allylic handle. Guibé et al. (1989), 30 TETRAHEDRON LETT. 2641–2644; Loffet et al. (1990), in PEPTIDES: CHEMISTRY, STRUCTURE AND BIOLOGY: PROCEEDINGS OF THE ELEVENTH AMERICAN PEPTIDE SYMPOSIUM 1015–1016 (Rivier and Marshall, eds.). This handle was cleaved by hydrostannolysis with Bu$_3$SnH. Subsequently, Albericio investigated cleavage conditions for the two allylic anchoring groups described by Kunz and Frank, 4-bromocrotonic acid and 4-trityloxy-but-(Z)-2-enyloxyacetic acid. Lloyd-Williams et al. (1991), 33 TETRAHEDRON LETT. 4207–4210. Albericio found that carrying out the cleavage reaction by treatment of the allylic anchor group with THF:dimethylsulfoxide (DMSO):0.5M HCl (2:2:1) using morpholine as a acceptor and Pd(PPH$_3$)$_4$ as a catalyst gave optimal results.

Hudson and Loffet independently investigated the use of the allyl group in solid-phase peptide synthesis as a side-chain protecting group. Biancalana et al. (1992), in INNOVATION AND PERSPECTIVES IN SOLID PHASE SYNTHESIS: PEPTIDES, POLYPEPTIDES, AND OLIGONUCLEOTIDES 135–152 (Epton, ed.); Lyttle and Hudson (1992), in PEPTIDES—CHEMISTRY AND BIOLOGY: PROCEEDINGS OF THE TWELFTH AMERICAN PEPTIDE SYMPOSIUM 583–584 (Smith and Rivier, eds.); Loffet and Zhang (1992), in INNOVATION AND PERSPECTIVES IN SOLID PHASE SYNTHESIS: PEPTIDES, POLYPEPTIDES, AND OLIGONUCLEOTIDES, 77–82 (Epton, ed.). The mild conditions to deprotect allyl functions were compatible with classical Fmoc/tert-butyl(tBu)-based methods and thus provided third dimension of orthogonality to protection schemes for the construction of peptides.

Recently, Albericio et al. reported the preparation of "head-to-tail" cyclic peptides, side-chain lactam peptides, glyco- and sulfo-peptides and branched peptides via a three-dimensional orthogonal solid-phase strategy involving the use of Fmoc, tBu and allyl protecting groups. Albericio et al. (1993), in PEPTIDES 1992: PROCEEDINGS OF THE TWENTY-SECOND EUROPEAN PEPTIDE SYMPOSIUM, (Schneider and Eberle, eds.); Kates et al. (1993), 34 TETRAHEDRON LETT. 1549–1552. As the studies described therein were nearing completion, an identical strategy was reported by Trzeciak and Bannwarth using allyl chemistry to prepare head-to-tail cyclic peptides. Trzeciak and Bannwarth (1992), 32 TETRAHEDRON LETT. 4557–4660.

Use of Allyl Deprotection Chemistry in Conjunction with Polyethylene Glycol-Polystyrene Graft Supports for Solid-Phase Synthesis A novel family of polyethylene glycol-polystyrene (PEG-PS) graft supports has recently been described by Barany. These supports improve synthetic efficiency and the range of reactions which can be carried out on resin-bound peptide chains. Barany et al. (1993) in PEPTIDES 1992: PROCEEDINGS OF THE TWENTY-SECOND EUROPEAN PEPTIDE SYMPOSIUM, (Schneider and Eberle, eds.); Barany et al. (1992), in PEPTIDES—CHEMISTRY AND BIOLOGY: PROCEEDINGS OF THE TWELFTH AMERICAN PEPTIDE SYMPOSIUM 603–604 (Smith and Rivier, eds.); Zalipsky et al. (1985), in PEPTIDES—STRUCTURE AND FUNCTION: PROCEEDINGS OF THE NINTH AMERICAN PEPTIDE SYMPOSIUM 257–260 (Deber et al., eds.). PEG-PS supports each have a defined and reproducible structure that comprises 20 to 70 weight-percent of polyethylene glycol. These supports swell appreciably in a range of solvents which are optimal for the stepwise assembly of peptide chains. PEG-PS supports have been used in either batchwise flow reactors or continuous-flow reactors with negligible back-pressure.

In order to extend the scope of these supports and their advantages in solid-phase peptide synthesis, deprotection of the allyl group on PEG-PS was explored. Several model peptides having the sequence Y-Ala-Xaa-Gln-Lys-Thr-Asp (OAl)-Thr-Pro-NH$_2$, where Xaa=Ala, Met, or Trp and Y=Fmoc or H, were prepared in parallel on PEG-PS and methylbenzhydrylamine (MBHA) resins using a 5-(4-(9-fluorenylmethyloxycarbonyl)aminomethyl-3,5-dimethoxyphenoxy)valeric acid (PAL) handle or linker to mediate attachment of the peptide to the support. These model peptides were used to examine conditions for the deprotection of the allyl group in conjunction with the suppression of oxidation of Met and of the back-alkylation of Trp.

The particulars of peptide synthesis were as follows:

Materials. Fmoc-Lys(Aloc)-OH, Fmoc-Asp(OAl)-OH and Fmoc-Asp-OAl were each prepared according to previously published procedures. Lyttle and Hudson (1992), in PEPTIDES—CHEMISTRY AND BIOLOGY: PROCEEDINGS OF THE TWELFTH AMERICAN PEPTIDE SYMPOSIUM 583–584 (Smith and Rivier, eds.); Belshaw et al. (1990), 20 SYN. COMM. 3157–3160). The rest of the Fmoc-amino acids and all other peptide synthesis reagents were obtained from Millipore Corporation. tBu was used for the protection of the side chain functional moieties of Asp, Glu, Thr, and Tyr; tert-butyloxycarbonyl (Boc) was used for Lys; and 2,2,5,7,8-pentamethylchroman-6-sulfonyl (Pmc) was used for Arg. The side chains of Asn, Gln, Trp were unprotected. All solvents were HPLC grade or of equivalent purity, and were used without further purification.

Peptide Synthesis: Standard Chain Elongation. Continuous flow solid-phase synthesis was carried out automatically using a Millipore 9050 Plus™ PepSynthesizer of the type shown in FIG. 1. Syntheses were carried out on an Fmoc-PAL-PEG-PS support (0.27 mmol Fmoc/g resin) unless otherwise indicated. The support was prepared according to a known procedure. Barany et al. (1993) in PEPTIDES 1992: PROCEEDINGS OF THE TWENTY-SECOND EUROPEAN PEPTIDE SYMPOSIUM, (Schneider and Eberle, eds.). The flow rate of the unit pump was set at 5.0 mL/min. Protected amino acid residues were added to the resin according to the following protocol: Fmoc group deprotection with 2% 1,8-diazobicyclo[5.4.0]-undec-7-ene (DBU) and 2% piperidine in N,N-dimethylformamide (DMF) for 7 min, followed by DMF washing for 12 min, followed by amino acid coupling for 30 min, followed by DMF washing for 8 min more. Thereafter, four equivalents each of Fmoc-amino acid and HOBt, along with sufficient benzotriazole-1-yl-oxy-tris(pyrrolidino)phosphonium hexafluorophosphate (PyBOP) to provide a final concentration of 0.3M, were dissolved in a solution of 0.6M N,N-diisopropylethylamine (DIEA) in DMF and delivered to the growing peptide support. Asn and Gln were incorporated as pentafluorophenyl esters in DMF (0.3M solution) containing four equivalents of HOBt. This process was repeated with the various preselected Fmoc-protected amino acids until the desired peptide was obtained.

Manual Allyl Deprotection. The general allyl deprotection conditions previously developed by Albericio and subsequently adapted by others were employed herein, with certain further refinements. Lloyd-Williams et al. (1991), 33 TETRAHEDRON LETT. 4207–4210; Biancalana et al. (1992), in INNOVATION AND PERSPECTIVES IN SOLID PHASE SYNTHESIS: PEPTIDES, POLYPEPTIDES, AND OLIGONUCLEOTIDES 135–152 (Epton, ed.). Side-chain deprotection of the allyl group was performed manually in a 5 mL polyproplene syringe fitted with a polyethylene disc and an inlet for Ar gas. In a typical study, the peptide attached to the resin (50 mg peptide resin, 15 µmol of peptide) was treated with Pd(PPh$_3$)$_4$ (50 mg, 43 µmol) and morpholine (50 µL, 0.57 mmol) in DMSO:THF:0.5N HCl (2:2:1, 2 mL total volume) for 2 h at 25° C. under Ar. The resin was washed at 2 min. per wash, three times successively with each of the following: THF, DMF, CH$_2$Cl$_2$, and 0.5% DIEA in CH$_2$Cl$_2$. Thereafter, the resin was washed three times with 0.02M sodium diethyldithio-carbamate in DMF at 15 min. per wash, five times with DMF at 2 min. per wash, and three times with CH$_2$Cl$_2$ at 2 min. per wash. In this manner, metal ions and other side-products were removed. The resin was then dried in vacuo. The dried resin was divided into two samples. Peptide-resin samples thus obtained were either first treated with piperidine-DMF following the above-described standard procedure to remove the Fmoc group, or washed with DMF prior to cleavage from the support.

Cleavage Conditions. Peptide-resin samples were treated with a mixture of TFA:anisole:β-mercaptoethanol (95:3:2), referred to as Reagent R, for 2 h. The filtrates were collected and the resin was further washed with TFA. Cold ether was added to the combined extracts and the solution was cooled to −70° C. After removing the supernatant, the obtained precipitate was washed several times with cold ether, dissolved in acetic acid and lyophilized.

Structural and Physical Analysis of Synthesized Peptides: Amino Acid Analysis. Peptides and peptide resins were hydrolyzed with gaseous hydrochloric acid (HCl). Bidlingmeyer et al. (1984), 336 J. CHROMATOGR. 93–104. Amino acid analysis were carried out using a Waters Femtotag™ chemical kit.

Mass Spectrometry. Mass spectra were recorded on a Waters prototype matrix assisted laser desorption (LD-MS) time-of-flight instrument.

HPLC. HPLC was carried out on a Waters apparatus with two 600 model solvent delivery systems, a Wisp 712 model automatic injector, a 490 model programmable wavelength UV detector or a 994 model programmable photodiode array detector and a 860 Networking Computer to control system operation and collect data. The HPLC analytical columns employed herein were Delta Pak C$_{18}$ (3.9×150 mm, 5 µm) 100 Å columns. Solution A for reverse-phase analysis was 0.1% trifluoroacetic acid (TFA) in H$_2$O and Solution B was 0.1% TFA in CH$_3$CN.

It is to be understood that the particular conditions and instrumentation described above represent one among many acceptable methods for carrying out peptide synthesis and manual allyl deprotection. Thus, the foregoing procedures are not be viewed as limiting in any way.

Analysis of the HPLC chromatograms of the model peptides obtained by the above-described protocol indicated that cleavage of the allyl protecting side-chain group occurred on both PEG-PS and PS supports. However, the purity of the peptide was greater when PEG-PS supports were used, as shown in FIG. 2. In the HPLC chromatogram tracings of each model peptide, a linear gradient was delivered over 30 min at a flow rate of 1.0 mL/min, with Solution B and Solution A at initial proportions of 1:9 and final proportions of 7:3. All peptides yielded the expected results upon LD-MS. Due to the incorporation of a large amount of polyethylene glycol, PEG-PS exists in a swollen state. The polyethylene glycol spacers of this resin allowed complete solubilization of reactive sites, resulting in a more efficient peptide synthesis reaction.

However, the conditions employed also yielded the undesired deprotection of the N$^\alpha$-Fmoc group in many cases. Deprotection of the N$^\alpha$-Fmoc group was not surprising since morpholine may act as a base. Furthermore, the use of DMSO as a solvent in the deprotection conditions proved incompatible with Met containing peptides. Although allyl deprotection was achieved, a second product, which was identified as that resulting from oxidation of the Met residue, was also obtained. The allyl deprotection conditions were compatible with Trp containing peptides because backalkylation of Trp was not observed, corroborating previously reported findings. Lyttle and Hudson (1992), in PEPTIDES—CHEMISTRY AND BIOLOGY: PROCEEDINGS OF THE TWELFTH AMERICAN PEPTIDE SYMPOSIUM 583–584 (Smith and Rivier, eds.). Lastly, the efficiency of the allyl deprotection was improved over tha reported by others when carried out in an inert atmosphere Obstacles Encountered in Adapting Allyl Protection Chem istry to Automated Synthesis Standard allyl deprotection according to the known an above-described techniques uses a solid palladium catalys suspended in an appropriate solvent and maintained in a inert atmosphere. This approach is not feasible when applie to a batch and continuous-flow peptide synthesizer, due t problems encountered with the delivery of the insolubl palladium catalyst to the reaction vessel. For example undesired solid by-products arising largely from the palla dium catalyst must be completely removed at the conclusio of the allyl deprotection step. Each of these consideration posed challenging obstacles to the development of an auto mated protocol that allowed for the removal of the allyl group in the same reaction column or vessel as that used for peptide elongation in an instrument of the type shown in FIG. 1. Automatable deprotection procedures were needed that could be implemented at any stage during the synthetic protocol.

Discovery of Allyl Deprotection Conditions Fully Compatible With Automation; Use of Same to Prepare Sensitive Glyco- and Sulfo-Peptides It was important that the selective deprotection conditions employed in an automated setting to remove the allyl group maintained full orthogonality with other protecting groups (e.g., Fmoc) and preserved labile amino acids (e.g., Met, Trp, Tyr($SO_3H$), as well as providing homogeneous reaction conditions readily adaptable to implementation on an automated peptide synthesizer. The present invention embodies the successful culmination of studies undertaken with the goal of developing a fully automatable allyl deprotection strategy that would fulfill these criteria. In particular, conditions have been discovered under which the palladium catalyst is soluble and undesired Fmoc deprotection is prevented. The now-described conditions are fully compatible with the synthesis of glyco- and sulfo-peptides. The present description of specific conditions and instrumentation represent one among many acceptable strategies for the practice of the present invention. Thus, the following account is not viewed as limiting the scope of the claimed invention in any way.

The continuous-flow Millipore 9050 Plus™ PepSynthesizer was modified as shown in FIG. 1 to accomodate the new conditions under which the allyl deprotection scheme of the present invention is carried out. Automation was still further facilitated by the use of software appropriate for the preparation of complex peptides according to the present invention. As described more fully below, the present synthetic protocol has been applied to the automated allyl group deprotection of acid, base, guanidino, hybroxyl, sulfhydryl and other functional groups present in the biologically relevant amino acids and derivatives thereof suitable for the synthesis of "head-to-tail" cyclic peptides, branched peptides and multiple antigenic peptide (MAPs). The studies which culminated in the present discovery of an automatable allyl deprotection strategy will now be more fully described.

The automated deprotection of allyl groups required initially that the problem of transferring the solid palladium catalyst to the reaction column and removing insoluble catalyst-derived side products be resolved. In situ automated allyl deprotection was expected to proceed with greater efficiency if the catalyst was in solution, avoiding a "solid-state" deprotection reaction. Moreover, it was forseeable that the presence of insoluble materials in the column or reaction vessel of an automated instrument would significantly complicate the delivery of solvents in subsequent steps, by introducing back-pressure. The solvent cocktail described by Albericio for use during the allyl deprotection step was biphasic and not homogeneous, in that the catalyst remained suspended in solid form. Lloyd-Williams et al. (1991), 33 TETRAHEDRON LETT. 4207–4210. For manual deprotections in which Ar was bubbled into the mixture according to the protocol described in the preceding section, the reaction was not adversely affected by the presence of a solid-state catalyst, since the solution was agitated efficiently. However, in an automated, continuous-flow instrument, such as the Millipore 9050 Plus™ PepSynthesizer, it is critical to have a homogeneous solution for equal dispersion of the deprotection solution on the resin.

To avoid a biphasic solution, an organic acid was required to replace the aqueous solution of 0.5M HCl. An organic acid that would be suitable to replace an aqueous solution of 0.5M HCl was HOAc. Accordingly, a mixture of DMSO:THF (1:1) containing 5% HOAc and 2.5% morpholine was prepared. This afforded a miscible solution that manually deprotected the allyl group on a model peptide having the sequence H-Ala-Met-Gln-Lys-Thr-Asp(OAl)-Thr-Pro-$NH_2$. This model peptide was prepared generally according to the protocol set forth above, with the present modification to the manual deprotection step.

With this modification, oxidation of the Met residue at position 7 of the model peptide was still observed. Therefore, the DMSO:THF (1:1) mixture was replaced with DMF. With this further modification, allyl deprotection with DMF containing 5% HOAc and 2.5% morpholine occurred without Met oxidation. Unfortunately, the catalyst remained insoluble in this mixture, precluding its use on an automated instrument.

The present catalyst, Pd(PPh$_3$)$_4$, is soluble in CHCl$_3$ and CH$_2$Cl$_2$, and is moderately soluble in benzene. Previous studies indicated that Pd(PPh$_3$)$_4$ was completely soluble in a solution of CHCl$_3$ containing 5% HOAc and 2.5% morpholine. This result was attractive since CHCl$_3$ was a solvent that was compatible with solid-phase peptide synthesis and PEG-PS. In a further modification, the model peptide was treated with Pd(PPh$_3$)$_4$ in a solution of CHCl$_3$ containing 5% HOAc and 2.5% morpholine. These conditions accomplished the deprotection of the allyl group, but still were not compatible with the N$^\alpha$-Fmoc group.

In subsequent efforts to eliminate unintended N$^\alpha$-Fmoc deprotection, morpholine was removed from the allyl deprotection solution. Treatment of the model peptide with Pd(PPh$_3$)$_4$ in a solution of CHCl$_3$ containing 5% HOAc afforded the desired unprotected peptide and an uncharacterized product. This result suggested that morpholine was not acting predominantly as a acceptor, but as a base that deprotected the N$^\alpha$-Fmoc group.

Accordingly, in a final modification of the allyl deprotection conditions, morpholine was replaced with a tertiary amine, N-methylmorpholine (NMM). Treatment of the model peptide with Pd(PPh$_3$)$_4$ in a solution of CHCl$_3$ containing 5% HOAc and 2.5% NMM afforded the unprotected peptide and concomitantly preserved the N$^\alpha$-Fmoc group. This successful result suggested that if an acceptor was required for the allyl deprotection to occur, contaminants or byproducts from the catalyst were the primary source.

From the foregoing modifications and refinements of the conditions under which allyl deprotection was carried out, the deprotection protocol set forth below and in the Representative Example emerged as the successful, fully automatable culmination of the present studies. The preferred automatable allyl deprotection protocol of the present invention has been integrated with the previously described linear peptide synthetic procedures, which are otherwise suitable for automation on a Millipore 9050 Plus™ PepSynthesizer, and fully automated peptide syntheses have been carried out thereon using allyl protected amino acid derivatives.

The strategy employed for automation was to treat Pd(PPh$_3$)$_4$ as a standard amino acid and store the catalyst in an amino acid-vial. The vial was purged with Ar and sealed in order to maintain an inert atmosphere. The preferred allyl deprotection solution of the present invention, i.e., CHCl$_3$ containing 5% HOAc and 2.5% NMM, was deployed in Syringe 3 and delivered to the amino acid vial containing Pd(PPh$_3$)$_4$. The resultant mixture was then subjected to at least one bubbling cycle to ensure that the catalyst was completely dissolved (solubilized) before delivery to the reaction column. The allyl deprotection solution was recycled through the column for about 2 h. The use of Syringe 3 for allyl deprotection required that Syringe 2 be loaded with reagents suitable for single activation chemistry for subsequent elongation of the peptide chain. For the production of cyclic peptides (described below), Syringe 2 is loaded with DIEA, and phosphonium or uronium salts are used for activation during both peptide elongation and the cyclization step. The phosphonium and uronium salts described in U.S. Ser. No. 07/766,895 are suitable for this purpose. The Auxiliary (Aux) bottle, shown in the upper right corner of the Synthesis Module (FIG. 1) contained a solution of 0.5% DIEA and 0.5% sodium diethyldithiocarbamate in DMF to remove side-products that can provoke back-pressure. This solution was delivered to the reaction column following the recycle. In the manual deprotection protocol set forth above, the resin was washed with separate solutions of 0.5% DIEA in $CH_2Cl_2$ and 0.5% sodium diethyldithiocarbamate in DMF. These two solutions have been combined in the present automated deprotection strategy, and no adverse effects have been detected. A final DMF wash was used prior to continuation of the synthetic protocol. The Representative Example set forth below illustrates one specific protocol for implementing allyl deprotection strategy of the present invention.

When the automated deprotection protocol set forth in the Representative Example was employed, no reagent afforded side-products were observed during the synthesis of model peptides. Furthermore, different sources and lots of $Pd(PPh_3)_4$ afforded similar results, indicating that the nucleophilic species was related to the palladium catalyst itself, rather than arising from contaminants therein.

Glyco- and sulfo-peptides present particularly difficult synthetic considerations. Albericio et al. (1993), in PEPTIDES 1992: PROCEEDINGS OF THE TWENTY-SECOND EUROPEAN PEPTIDE SYMPOSIUM. (Schneider and Eberle, eds.). Accordingly, there was keen interest in the applicability of the present automated allyl deprotection strategy to the synthesis of these difficult peptides.

For the synthesis of sulfated tyrosine peptides, removal of the allyl group requires mild cleavage conditions. The sensitive sulfur-oxygen bond proved unstable to the use of 0.5M HCl as a proton source according to known deprotection methods. The present conditions of $Pd(PPh_3)_4$ catalyzed deprotection in a solution of $CHCl_3$ containing 5% HOAc and 2.5% NMM, applied in a synthetic protocol generally as set forth above and together with a peptide amide linker that requires mild cleavage conditions {|5-|(9-fluorenylmethyloxycarbonyl)aminoxanthen-2-oxy) valeric acid, referred to as XAL}, provided a method for the synthesis of sulfated peptides. With regard to the synthesis of glyco- and sulfo-peptides, see also Botems et al. (1992), in PEPTIDES—CHEMISTRY AND BIOLOGY: PROCEEDINGS OF THE TWELFTH AMERICAN PEPTIDE SYMPOSIUM 601–602 (Smith and Rivier, eds.); Han et al. (1993) in PROCEEDINGS OF THE FIRST CHINESE PEPTIDE SYMPOSIUM in press (Yu-cang, ed.).

Use of the Present Automatable Allyl Deprotection Strategy in the Synthesis of Cyclic Peptides In order to further demonstrate the effectiveness of the present automatable allyl deprotection conditions, the allyl strategy of the present invention was applied to the automated synthesis of a cyclic peptide. Rovero recently published the synthesis of the tachykinin antagonist peptide MEN 10355, cyclo(Asp-Tyr-D-Trp-Val-D-Trp-D-Trp-Arg). Rovero (1991), 32 TETRAHEDRON LETT. 2639–2642.

Figure 3:
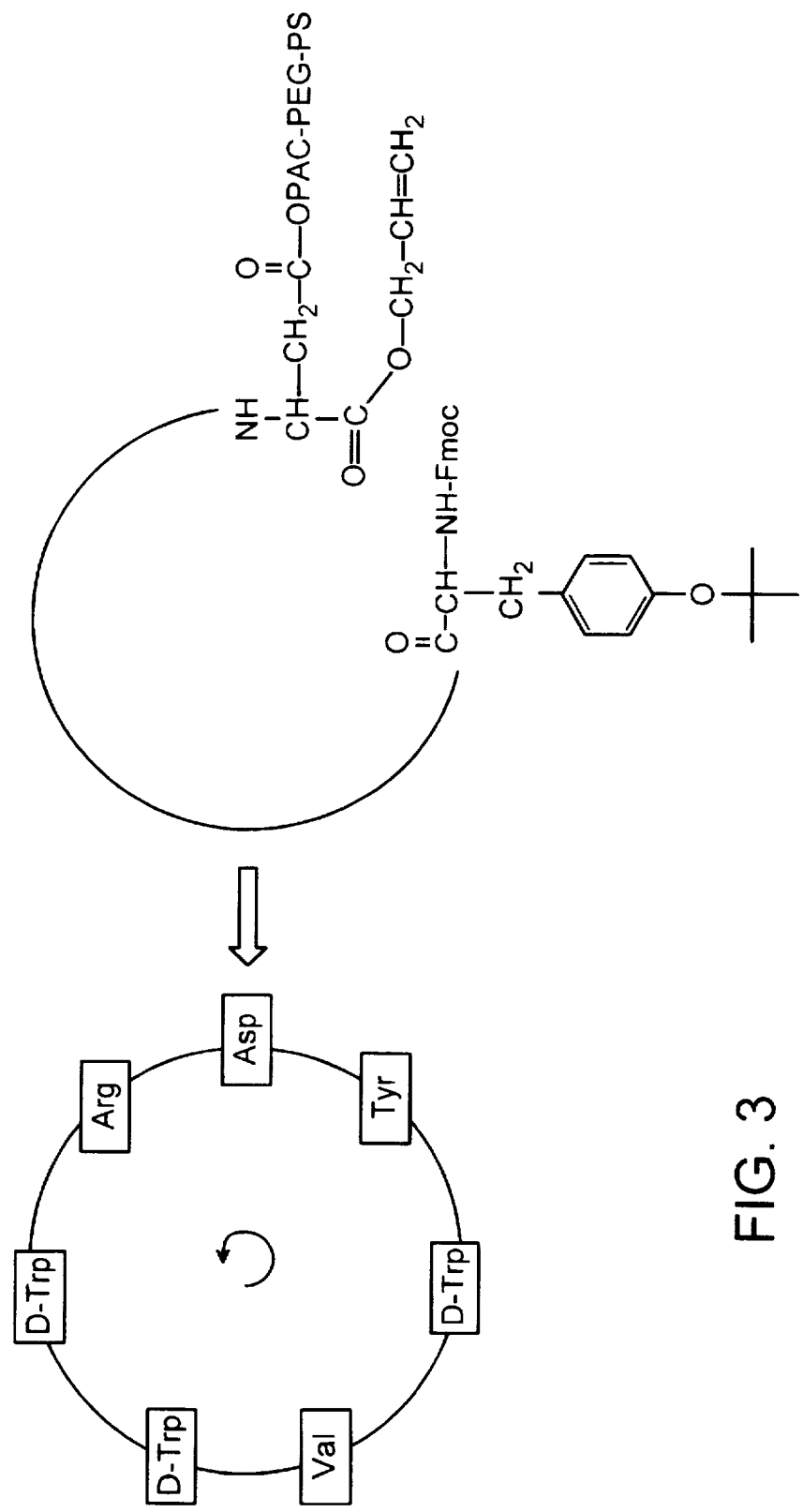
FIG. 3 schematically illustrates the retrosynthetic analysis of tachykinin antagonist peptide.

This was chosen as a model head-to-tail cyclic peptide. The approach selected for the synthesis of this cyclic heptapeptide was based on the automated allyl deprotection strategy outlined above, and is schematically illustrated in FIG. 3.

A linear synthesis of the model cyclic peptide was carried out using a combined Fmoc/tBu protection strategy generally according to the procedures set forth above, in conjunction with an Fmoc-Asp(O-PAC-PEG-PS)-OAl starting resin. PAC refers to the p-alkoxybenzyl alcohol handle employed for attachment of the peptide to the PEG-PS support. To synthesize the present model tachykinin antagonist peptide, an $N^\alpha$-Fmoc, $C^\alpha$-allyl protected Asp derivative was linked to the PAC handle through the side-chain carboxy function. Upon completion of linear synthesis, deprotection of the $C^\alpha$-allyl protecting group was accomplished with the preferred solution of $Pd(PPh_3)_4$ in $CHCl_3$ containing 5% HOAc and 2.5% NMM.

Automated cyclization was thereupon carried out according to the following protocol:

Automated Cyclization. The present protocol is an adaptation of the original method of Felix et al. for resin-bound cyclization for use with allyl-deprotected peptides in an automated setting. Felix et al. (1988), 31 INT. J. PEPTIDE PROTEIN RES. 231–238. Following $N^\alpha$-Fmoc deprotection of the final amino acid, four equivalents of HOBt and PyBOP, stored in the amino acid vial positioned after the one corresponding to the palladium catalyst (see FIG. 1), was dissolved to a final concentration of 0.3M in a solution of 0.6M DIEA in DMF, delivered from Syringe 2. The resultant solution was delivered to the allyl deprotected, support-bound peptide. Cyclization was allowed to proceed until ninhydrin negative, followed by a DMF wash (15 sec, 3 mL/min) and a $CH_2Cl_2$ wash (6 min, 3 mL/min).

Figure 4:
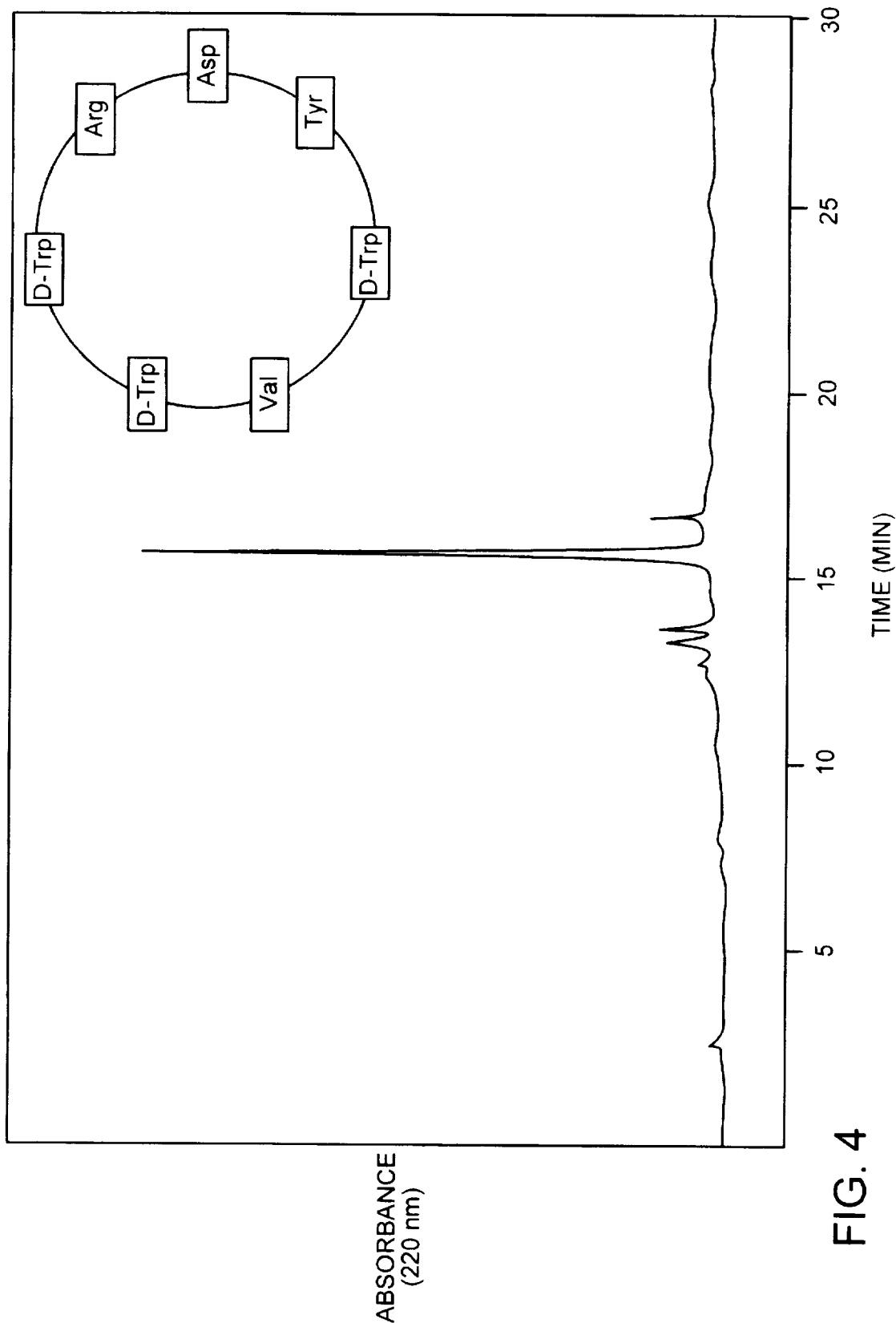
FIG. 4 includes the HPLC chromatogram tracing of a crude model cyclic peptide (inset) directly after cleavage from a PEG-PS support.

Following $N^\alpha$-Fmoc removal, PyBOP-HOBt-DIEA-mediated cyclization, and removal of tBu side-chain protecting groups, the cyclic peptide was released from the support according to the cleavage protocol presented herein. The purity of the cyclic peptide thus obtained was similar to that obtained by performing the cyclization manually. An HPLC chromatogram tracing of the model head-to-tail cyclic peptide prepared according to the present automated procedures is shown in FIG. 4. The tracing is that of the crude deprotected cyclic peptide immediately after cleavage from the support, upon exposure to a linear gradient in which the relative proportions of Solution B and Solution A were adjusted from 1:3 to 11:9 at a flow rate of 1.0 mL/min delivered over 30 min. LD-MS analysis of the crude cyclic peptide yielded a mass equivalent ($MH^+$) of 1092.3 daltons.

Figure 5:
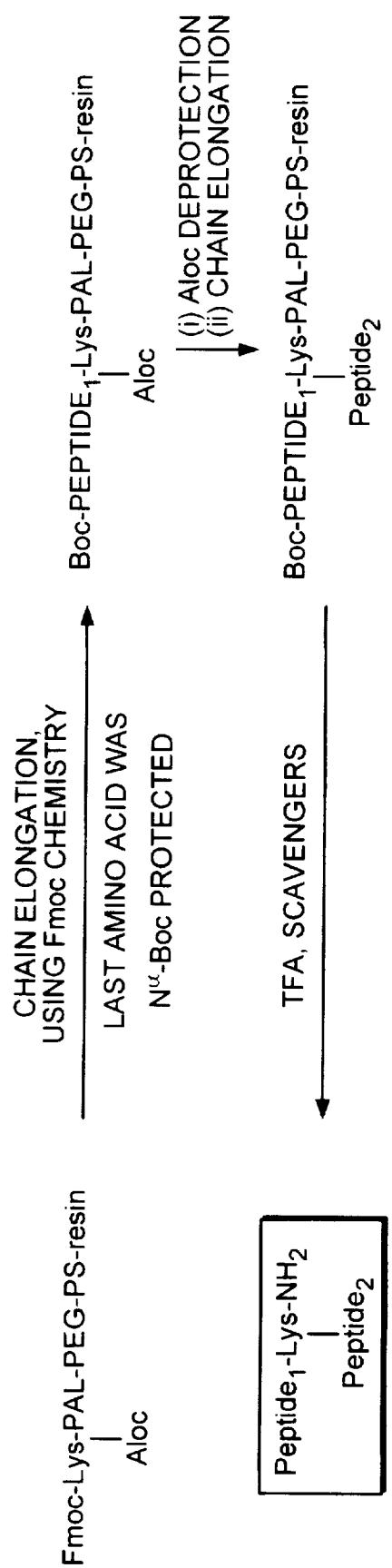
FIG. 5 schematically illustrates a general strategy for the preparation of a branched peptide.

Use of the Present Automatable Allyl Deprotection Strategy in the Synthesis of Branched Peptides The automated allyl deprotection strategy of the present invention is also applicable to the synthesis of branched peptides of the type shown in FIG. 5. To illustrate this aspect of the invention, an Fmoc-Lys(Aloc)-PAL-PEG-PS resin was prepared. A linear synthesis of prothrombin was performed generally according to the previously-discussed protocol, using a combined Fmoc/tBu strategy for conventional peptide elongation. Next, side-chain deprotection of the Aloc group of Lys was accomplished with $Pd(PPh_3)_4$ in the preferred solution of $CHCl_3$ containing 5% HOAc and 2.5% NMM using the automated allyl deprotection procedures described below. A linear synthesis of Leu-enkephalin was subsequently performed by chain elongation from the epsilon amino group ($N^\epsilon$) of the side-chain of lysine. To ensure elongation at the desired (side-chain) site, the last amino acid of prothrombin (Ala at position 9) was $N^\alpha$-Boc protected during the synthesis of Leu-enkephalin.

Thus, branched peptides may be synthesized according to the present invention by integrating the following protocol with the automated allyl deprotection and peptide synthesis techniques described herein:

Synthesis of Branched Peptides. The final amino acid of the first branch was $N^{\alpha}$-protected with a Boc rather than an Fmoc group in order to prevent further elongation of the initial chain. After attachment of the Boc-amino acid to the resin-bound peptide, the allyl side chain protecting group was removed using the automated allyl deprotection conditions disclosed herein. All subsequent couplings of the second branch polypeptide were carried out according to the linear synthesis protocol described above, except the first amino acid of the second branch was coupled for 45 min.

Figure 6:
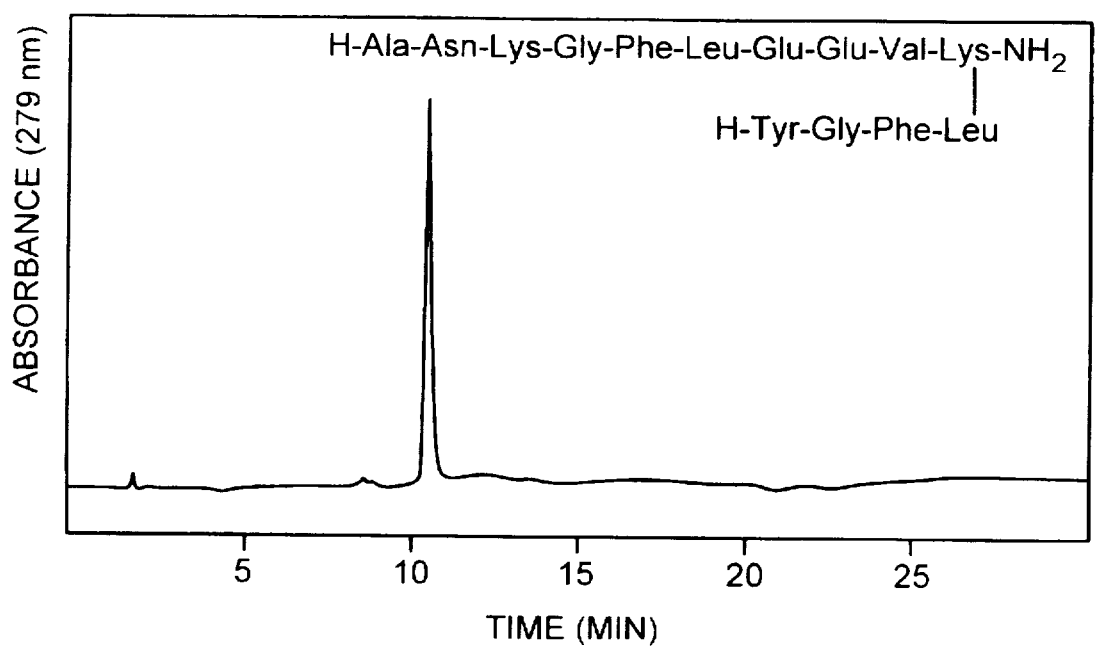
FIG. 6 includes the HPLC chromatogram tracing of a crude branched peptide (inset) directly after cleavage from the support.

The resulting exemplary branched peptide was released from the resin generally by the cleavage protocol disclosed herein. Removal of the tBu side-chain protecting groups and $N^{\alpha}$-Boc group yielded the desired branched peptide, $C^{\alpha}$-(prothrombin)-$N^{\epsilon}$-(Leu-enkephalin)-Lys-$NH_2$. An HPLC chromatogram tracing of this product, obtained in crude form and analyzed immediately following release from the resin, is shown in FIG. 6. The tracing was generated by exposure of the crude branched peptide to a linear gradient in which the relative proportions of Solution B and Solution A were adjusted from 1:9 to 9:1, over 30 min at a flow rate of 1.0 mL/min. LD-MS analysis of the crude branched peptide yielded a mass equivalent ($MH^+$) of 1671.3 daltons. Use of the Present Automatable Allyl Deprotection Strategy in the Synthesis of Multiple Antigenic Peptides The success and ease of synthesizing branched peptides, discussed above, illustrated that the present strategy was well-suited to the synthesis of multiple antigenic peptides, known as MAPs. Tam (1988.), 85 PROC. NATL. ACAD. SCI. USA 5409–5413; Tam et al. (1990), 171 J. EXP. MED. 299–306). MAPs are employed to produce peptide immunogens without the use of a protein carrier, such as bovine serum albumin, thyroglobulin or keyhole limpet hemocyanin. Instead, a small branched lysine core matrix is used to amplify the peptide antigen to multiple copies.

For the preparation of a MAP containing one epitope, Boc-Lys(Boc)-OH and Fmoc-Lys(Fmoc)-OH can be used for Boc and Fmoc chemistry, respectively, according to the procedures described herein. The current strategy for obtaining MAPs containing two epitopes requires Boc chemistry, since Fmoc-Lys(Boc)-OH is necessary.

Figure 7:
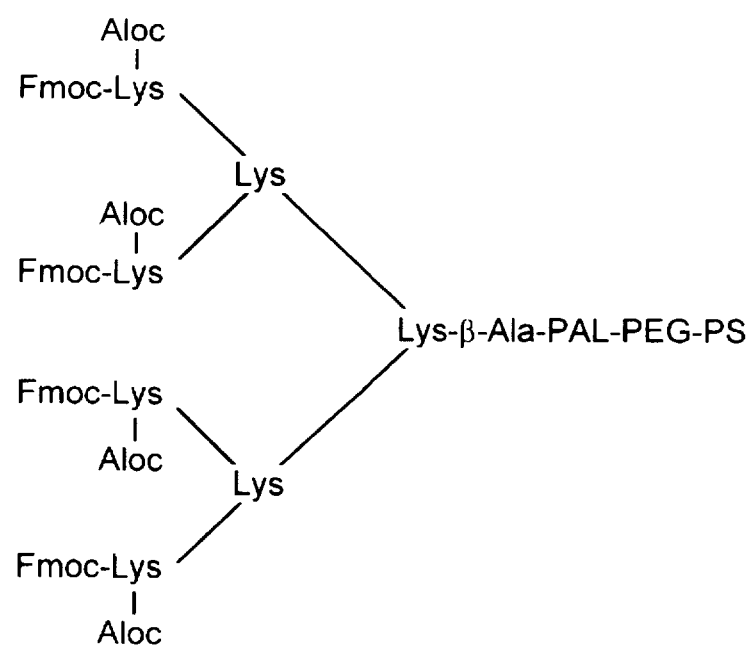
FIG. 7 schematically depicts a PEG-PS resin having bound thereto a multiple antigenic peptide (MAP) core suitable for the production of a two epitope MAP.

With the strategy of the present invention, the preparation of MAPs containing two epitopes can be achieved and automated with Fmoc chemistry, using a core matrix of the general type shown in FIG. 7. To illustrate this application of the present allyl deprotection strategy, an [Fmoc-Lys(Aloc)]$_4$-β-Ala-PAL-PEG-PS core resin was prepared. A linear synthesis of prothrombin using Fmoc/tBu protection was carried out as described in the previous section, followed by side-chain deprotection of the Aloc group using the automated allyl deprotection conditions described below of Lys and linear extension of Leu-enkephalin from the $N^{\epsilon}$ group of lysine. These procedures yielded the desired two-epitope MAP.

Representative Example

The preferred automated allyl deprotection strategy of the present invention has been carried out according to the following protocol, which has been used in conjunction with the automatable peptide synthesis procedures described above:

Automated Deprotection. The PepSynthesizer was configured for allyl deprotection as shown in FIG. 1. In a typical synthesis, the Pd(PPh$_3$)$_4$ catalyst (125 mg, 108 µmol) was stored in an amino acid vial which was sealed under Ar. The vial containing the catalyst was positioned in the amino acid module following the last amino acid of the sequence. The catalyst was dissolved in Syringe 3 (depicted at the lower left of the Synthesis module in FIG. 1) to a final concentration of 0.14M with a solution of 5% HOAc and 2.5% N-methylmorpholine (NMM) in CHCl$_3$. Twenty bubble cycles were used to completely dissolve the catalyst. The resulting allyl deprotection solution was delivered to the peptide resin (500 mg, 0.3 mmol/g) and allowed to recycle through the column for 2 h. The column was then washed with a solution of 0.5% DIEA and 0.5% sodium diethyldithiocarbamate in DMF (delivered from the Aux bottle, 10 min, 6 mL/min) and DMF (10 min, 6 mL/min) to prepare the support for the next cycle of synthesis.

Relevant parameters of this representative protocol are summarized as follows:

TABLE 1

| Operation | Solvent/Reagents | Duration |
| --- | --- | --- |
| Dissolve Pd complex | 5% HOAc and 2.5% NMM in CHCl$_3$ | 5 min |
| Remove allyl group | Recycle Pd complex solution | 2 h |
| Flush Pd solution | 0.5% DIEA and 0.5% Sodium diethyldithiocarbamate | 10 min |
| Flush Pd wash solution | DMF | 10 min |

EQUIVALENTS

Those skilled in the art will recognize, or be able to ascertain using no more than routine experimentation, many equivalents to the specific embodiments of the invention described herein. These and all other such equivalents are intended to be encompassed by the following claims.

We claim:

1. A method for selectively removing an allyl protecting group from an allyl-protected derivative of a biologically relevant amino acid or from a peptide derivative in which said biologically relevant amino acid is one component, comprising the steps of:

a) providing to an allyl-protected peptide derivative or amino acid derivative bound to a solid support a single phase liquid solution comprising an organopalladium catalyst dissolved in a single phase liquid solvent mixture, said single phase liquid solvent mixture comprising a solvent, a carboxylic acid and an acceptor selected from the group consisting of dimedone, N-methylaniline, N,N'-dimethylbarbituric acid, morpholine and N-methylmorpholine, wherein the carboxylic acid is chosen such that:
      i) protecting groups attached to the peptide derivative or amino acid derivative remain stably attached thereto when the allyl-protecting group is removed; and
      ii) functional groups within the peptide derivative or amino acid derivative remain unreactive when the allyl protecting group is removed;

b) contacting said single phase liquid solution with the allyl-protected peptide derivative or amino acid derivative;

c) incubating the allyl-protected peptide derivative or amino acid derivative with said single phase liquid solution for a sufficient period of time for the allyl-protecting groups to be catalytically removed from the peptide derivative or amino acid derivative, such that an allyl-deprotected peptide derivative or amino acid derivative is obtained; and d) separating the allyl-deprotected peptide derivative or amino acid derivative from the single phase liquid solution.

2. The method of claim 1 wherein the organopalladium catalyst is an organopalladium (0) catalyst.

3. The method of claim 2 wherein the organopalladium catalyst is tetrakistriphenylphosphine palladium (0).

4. The method of claim 1 wherein the organopalladium catalyst is tetrakistriphenylphosphine palladium (0), and wherein steps (a)–(c) are carried out in an inert atmosphere.

5. The method of claim 1 wherein the solvent is chloroform, methylene chloride or benzene.

6. The method of claim 1 wherein the carboxylic acid is formic acid, acetic acid or propionic acid.

7. The method of claim 1 wherein the organopalladium catalyst is tetrakistriphenylphosphine palladium (0), said catalyst being provided in a solvent mixture comprising acetic acid, N-methylmorpholine and chloroform, said catalyst being provided in an inert atmosphere.

8. The method of claim 7 wherein said single phase liquid solvent mixture comprises about 5% acetic acid, about 2.5% N-methylmorpholine and chloroform.

9. A method for selectively removing an allyl protecting group from an allyl-protected derivative of a biologically relevant amino acid or from a peptide derivative in which said biologically relevant amino acid is one component, comprising the steps of:

a) providing to an allyl-protected peptide derivative or amino acid derivative bound to a solid support a single phase liquid solution comprising tetrakistriphenylphosphine palladium (0) catalyst dissolved in a single phase liquid solvent mixture, said single phase liquid solvent mixture further comprising acetic acid, N-methylmorpholine and chloroform, said catalyst further being provided under an inert atmosphere;

b) contacting said single phase liquid solution with the allyl-protected peptide derivative or amino acid derivative under an inert atmosphere;

c) incubating the allyl-protected peptide derivative or amino acid derivative with said single phase liquid solution under an inert atmosphere for a sufficient period of time for the allyl protecting group to be catalytically removed from the peptide derivative or amino acid derivative, such that an allyl-deprotected peptide derivative or amino acid derivative is obtained; and d) separating the allyl-deprotected peptide derivative or amino acid derivative from the single phase liquid solution.

10. The method of claim 9 wherein said single phase liquid solvent mixture comprises about 5% acetic acid, about 2.5% N-methylmorpholine and chloroform.

11. The method of claim 9 wherein the allyl-protected derivative of a biologically relevant amino acid is a derivative of alanine, arginine, asparagine, aspartic acid, cysteine, glutamine, glutamic acid, glycine, histidine, isoleucine, leucine, lysine, methionine, ornithine, phenylalanine, proline, serine, threonine, tryptophan, tyrosine or valine.

12. The method of claim 11 wherein the $N^\alpha$ functional group of said allyl-protected derivative of a biologically relevant amino acid is protected by an allyl group.

13. The method of claim 11 wherein the allyl-protected derivative of said biologically relevant amino acid is further protected by a tert-butyl, tert-butyloxycarbonyl, tert-amyloxycarbonyl, adamantanyloxycarbonyl, 9-fluorenylmethyloxycarbonyl, 2-(3,5-dimethoxyphenyl)-2-propyloxycarbonyl, dithiasuccinoyl, biphenylylisopropyloxycarbonyl, 2,2,5,7,8-pentamethylchroman-6-sulfonyl or phenylisopropyloxycarbonyl group.

14. The method of claim 9 wherein the allyl-protected derivative of a biologically relevant amino acid is a derivative of arginine, asparagine, aspartic acid, cysteine, glutamine, glutamic acid, histidine, lysine, methionine, ornithine, serine, threonine, or tyrosine, the side-chain functional group of which is protected by an allyl protecting group, and the $N^\alpha$ functional group of which is protected by a tert-butyl, tert-butyloxycarbonyl, tert-amyloxycarbonyl, adamantanyloxycarbonyl, 9-fluorenylmethyloxycarbonyl, 2-(3,5-dimethoxyphenyl)-2-propyloxycarbonyl, dithiasuccinoyl, biphenylylisopropyloxycarbonyl, 2,2,5,7,8-pentamethyl-chroman-6-sulfonyl or phenylisopropyloxycarbonyl group.

15. The method of claim 9 wherein the allyl-protected derivative of a biologically relevant amino acid is a side-chain sulfated, glycosylated, phosphorylated, iodinated, alkylated, or lipidated derivative of arginine, asparagine, aspartic acid, cysteine, glutamine, glutamic acid, histidine, lysine, methionine, ornithine, serine, threonine or tyrosine, wherein said modified amino acid side-chain is protected by an allyl protecting group, further wherein the $N^\alpha$ functional group of said amino acid derivative is protected by a tert-butyl, tert-butyloxycarbonyl, tert-amyloxycarbonyl, adamantanyl-oxycarbonyl, 9-fluorenylmethyloxycarbonyl, 2-(3,5-dimethoxyphenyl)-2-propyloxy-carbonyl, dithiasuccinoyl, biphenylylisopropyloxycarbonyl, 2,2,5,7,8-pentamethylchroman-6-sulfonyl or phenylisopropyloxycarbonyl group.

16. The method of claim 9 wherein the allyl-protected derivative of a biologically relevant amino acid is attached to a solid support.

17. The method of claim 16 wherein the $N^\alpha$ functional group of said allyl-protected derivative of a biologically relevant amino acid is protected by an allyl group, said allyl group mediating attachment of the protected amino acid derivative to the solid support.

18. The method of claim 16 wherein the solid support is a polyethylene glycol-polystyrene graft copolymer support or a polystyrene support.

19. The method of claim 16 wherein the allyl-protected derivative of a biologically relevant amino acid is attached to a solid support through a 5-(4-(9-fluorenylmethyloxycarbonyl)-aminomethyl-3,5-dimethoxyphenoxy)valeric acid, 5-[(9-fluorenylmethyloxycarbonyl)aminoxanthen-2-oxy]valeric acid or p-alkoxybenzyl alcohol linker or handle.

20. The method of claim 16 wherein the allyl-protected derivative of a biologically relevant amino acid is present in a synthesized peptide formed of biologically relevant amino acid residues linked together by peptide bonds.

21. A method of claim 9 wherein the allyl-protected derivative of a biologically relevant amino acid is present in a synthesized peptide formed of biologically relevant amino acid residues linked together by peptide bonds, said peptide being attached to a polyethylene glycol-polystyrene graft copolymer support through a 5-(4-(9-fluorenylmethyloxycarbonyl)aminomethyl-3,5-dimethoxy-phenoxy)valeric acid handle or linker, said peptide having been formed from biologically relevant amino acid derivatives, the $N^\alpha$ functional groups of which were protected by 9-fluorenylmethyloxycarbonyl groups or allyl groups.

22. A method for selectively removing an allyl protecting group from an allyl-protected derivative of a biologically relevant amino acid or from a peptide derivative in which said biologically relevant amino acid is one component, comprising the steps of:

a) providing to an allyl-protected peptide derivative or amino acid derivative bound to a solid support a single phase liquid solution comprising an organopalladium catalyst dissolved in a single phase liquid solvent mixture, said single phase liquid solvent mixture comprising a solvent, a carboxylic acid and N-methylmorpholine, wherein the carboxylic acid is chosen such that:

i) protecting groups attached to the peptide derivative or amino acid derivative remain stably attached thereto when the allyl-protecting group is removed; and ii) functional groups within the peptide derivative or amino acid derivative remain unreactive when the allyl protecting group is removed;

b) contacting said single phase liquid solution with the allyl-protected peptide derivative or amino acid derivative;

c) incubating the allyl protected peptide derivative or amino acid with said single phase liquid solution for a sufficient period of time for the allyl protecting groups to be catalytically removed from the peptide derivative or amino acid derivative, such that an allyl-deprotected peptide derivative or amino acid derivative is obtained; and d) separating the allyl-deprotected peptide derivative or amino acid derivative from the single phase liquid solution.

* * * * *

UNITED STATES PATENT AND TRADEMARK OFFICE
CERTIFICATE OF CORRECTION

PATENT NO. : 5,777,077
DATED : July 7, 1998
INVENTOR(S) : Albericio et al.

Figure 2A:
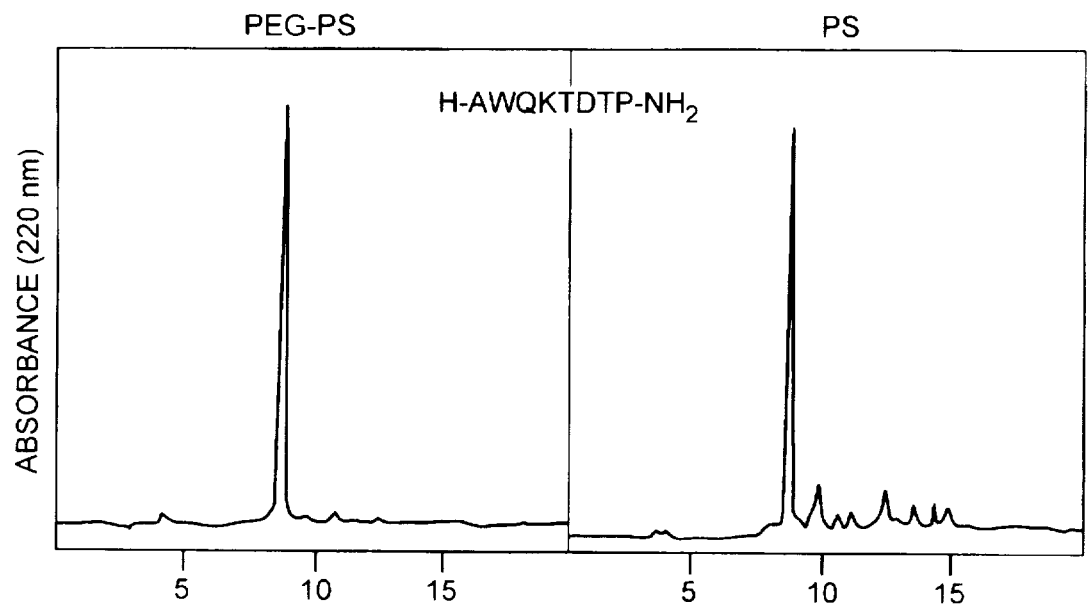
FIG. 2 includes high-pressure liquid chromatography (HPLC) chromatogram tracings comparing manual allyl deprotection of model peptides on a polyethylene glycol-polystyrene graft (PEG-PS, left hand column) support with manual allyl deprotection on a polystyrene (PS, right hand column) support for: H-AWQKTDTP-NH$_2$ (row A); H-AMQKTDTP-NH$_2$ (row B); H-AAQKTDTP-NH$_2$ (row C).
Figure 2B:
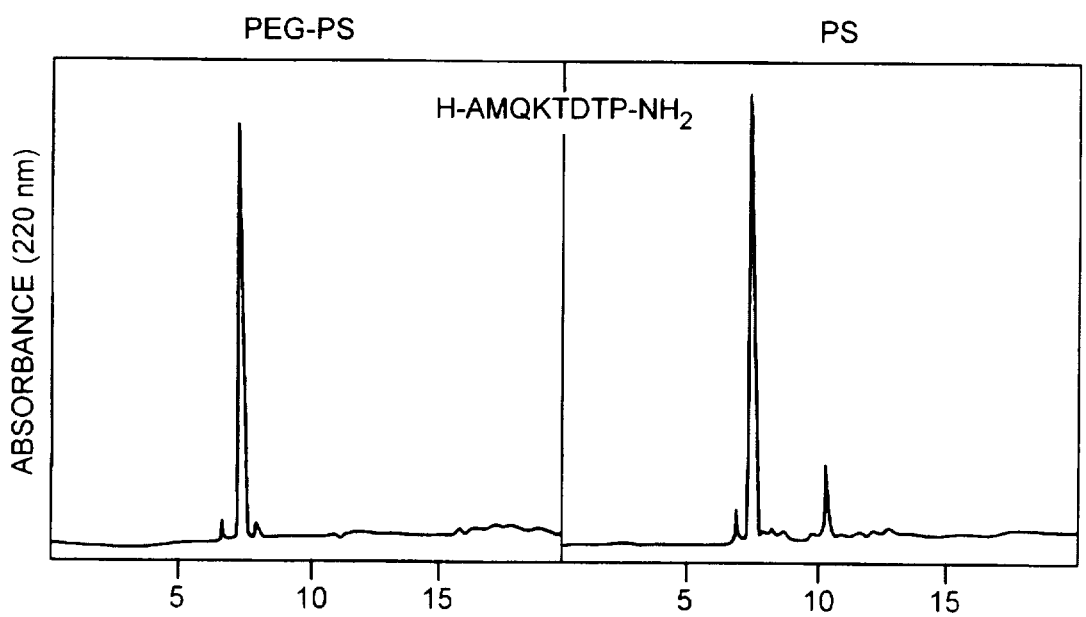
Figure 2C:
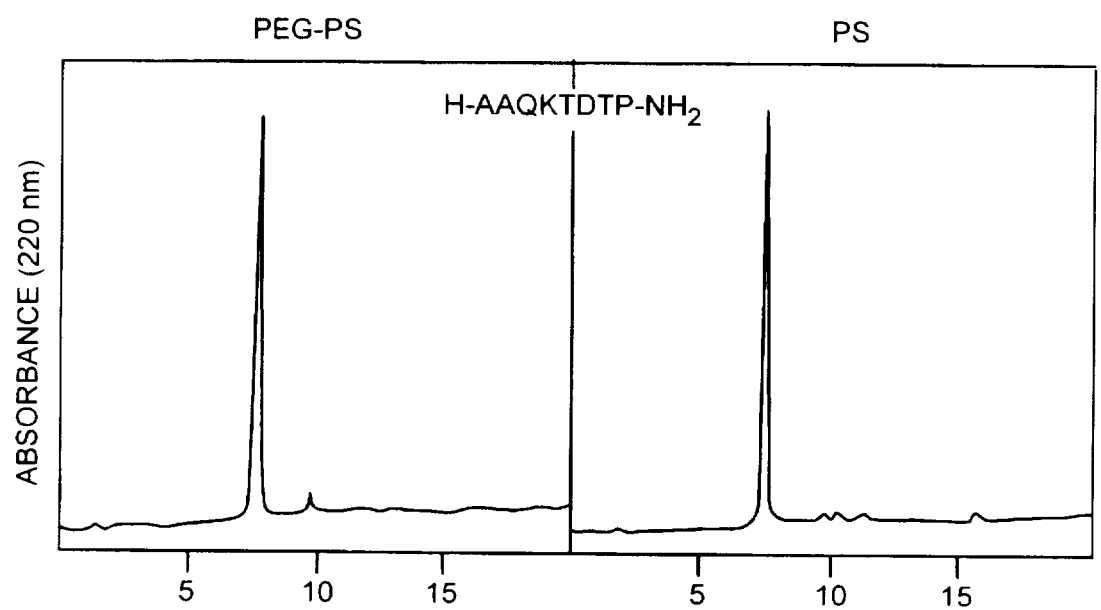

It is certified that error appears in the above-identified patent and that said Letters Patent is hereby corrected as shown below:

Col. 3, line 49, delete "Figure 2 includes" and insert therefor --Figures 2A to 2C include--.

Col. 3, line 52, after the word "PEG-PS" delete ", left hand column" and insert therefor --, left hand panel--.

Col. 3, lines 53-54, after the word "PS" delete ", right hand column" and insert therefor --right hand panel--.

Col. 3, lines 54-56, after the word "support" delete "for : H-AWQKTDTP-NH$_2$ (row A); H-AMQKTDTP-NH$_2$ (row B); H-AAQKTDTP-NH$_2$ (row C)" and insert therefor -- for : H-AWQKTDTP-NH$_2$ (FIG. 2A); H-AMQKTDTP-NH$_2$ (FIG. 2B); H-AAQKTDTP-NH$_2$ (FIG. 2C)--.

Signed and Sealed this

Sixteenth Day of March, 1999

Attest:

Attesting Officer

Q. TODD DICKINSON

Acting Commissioner of Patents and Trademarks